United States Patent [19]

Berg et al.

[11] Patent Number: 4,666,563

[45] Date of Patent: * May 19, 1987

[54] SEPARATION OF ISOPROPYL ETHER FROM ISOPROPANOL AND WATER BY EXTRACTIVE DISTILLATION

[76] Inventors: Lloyd Berg; An-I Yeh, both of 1314 S. Third Ave., Bozeman, Mont. 59715

[*] Notice: The portion of the term of this patent subsequent to Apr. 9, 2002 has been disclaimed.

[21] Appl. No.: 800,155

[22] Filed: Nov. 20, 1985

[51] Int. Cl.$^4$ .......................... B01D 3/40; C07C 41/42
[52] U.S. Cl. ......................................... 203/56; 203/64; 203/14; 568/699; 568/913
[58] Field of Search ...................... 203/56, 64, 14, 18; 568/699, 697, 913, 918

[56] References Cited

U.S. PATENT DOCUMENTS

| | | | |
|---|---|---|---|
| 1,442,520 | 1/1923 | Buc | 568/699 |
| 2,559,519 | 7/1951 | Smith et al. | 203/64 |
| 2,559,520 | 7/1951 | Smith et al. | 203/64 |
| 2,664,435 | 12/1953 | Burton et al. | 203/64 |
| 2,721,222 | 10/1955 | Cottle et al. | 568/699 |
| 2,927,064 | 3/1960 | Luzader et al. | 203/64 |
| 3,410,762 | 11/1968 | Dean | 203/64 |
| 4,469,491 | 9/1984 | Finkel | 203/64 |
| 4,510,022 | 4/1985 | Berg et al. | 203/64 |

FOREIGN PATENT DOCUMENTS 614470 2/1961 Canada ........................... 568/699

*Primary Examiner*—Wilbur Bascomb

[57] ABSTRACT

Isopropyl ether cannot be completely removed from isopropyl ether—isopropanol—water mixtures by distillation because of the presence of the minimum ternary azeotrope. Isopropyl ether can be readily removed from mixtures containing it, isopropanol and water by using extractive distillation in which the extractive distillation agent is a higher boiling glycol, glycol ether or a mixture of them. Typical examples of effective agents are ethylene glycol, propylene glycol, diethylene glycol diethyl ether plus propylene glycol ethyl ether.

9 Claims, No Drawings

SEPARATION OF ISOPROPYL ETHER FROM ISOPROPANOL AND WATER BY EXTRACTIVE DISTILLATION

FIELD OF THE INVENTION

This invention relates to a method for separating isopropyl ether from isopropanol using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus requires either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the component of highest vapor pressure. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The breaking of this azeotrope by extractive distillation is a new concept. One of the first applications of this concept might be the breaking of the ethanol-water azeotrope. J. Schneible, U.S. Pat. No. 1,469,447 used glycerol; P. V. Smith & C. S. Carlson, U.S. Pat. No. 2,559,519 employed ethoxyethanol and butoxyethanol for this purpose and W. E. Catterall, U.S. Pat. No. 2,591,672 reported gasoline as being effective. These are dehydrations and operate more conventionally as a solvent extraction process rather than an extractive distillation. Smith, U.S. Pat. No. 2,559,520 described an extractive distillation process for separating one alcohol from another alcohol, specifically ethanol from isopropanol. Finkel, U.S. Pat. No. 4,469,491 described an extractive distillation process for separating diisopropyl ether from similar boiling hydrocarbons.

The most common method of manufacturing isopropanol is by the hydration of propylene using sulfuric acid as the catalyst. However before the isopropanol can be removed from the reaction mixture, some of its reacts with the sulfuric acid to form isopropyl ether. Thus isopropanol made by this method invariably contains some isopropyl ether as an impurity. Normally a mixture of several solvents are separated and recovered by fractionation in a multiplate rectification column and the ease of separation depends upon the difference in boiling points of the compounds to be separated. However isopropanol, isopropyl ether and water form three binary azeotropes and one ternary azeotrope as shown in Table I. Thus any mixture containing these three compounds subjected to rectification will produce an overhead product boiling at 61.6° C. and containing 4.7% water, 7.3% isopropanol and 88% isopropyl ether.

TABLE I

| Azeotropes of Isopropyl Ether, Isopropanol and Water. | | | |
|---|---|---|---|
| Compounds | B.P., °C. | Azeotrope Composition, Wt. % | |
| Water | 100 | | |
| Isopropanol | 82.5 | | |
| Isopropyl ether | 69.0 | | |
| Water-Isopropanol | 80.3 | 12.6 | 87.4 |
| Isopropanol-Isopropyl ether | 66.2 | 16.3 | 83.7 |
| Water-Isopropyl ether | 62.2 | 4.5 | 95.5 |
| Water-Isopropanol-Isopropyl ether | 61.6 | 4.7 | 7.3 | 88.0 |

Extractive distillation would be an attractive method of effecting the separation of isopropyl ether from isopropanol and water if agents can be found that (1) will break the isopropyl ether-isopropanol-water azeotrope and (2) are easy to recover from the isopropanol and water, that is, form no azeotrope with isopropanol and boil sufficiently above isopropanol to make the separation by rectification possible with only a few theoretical plates.

Extractive distillation typically requires the addition of an equal amount to twice as much extractive agent as the isopropyl ether-isopropanol-water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation. Another consideration in the selection of the extractive distillation agent is its recovery from the bottoms product. The usual method is rectification in another column. In order to keep the cost of this operation to a minimum, an appreciable boiling point difference between the compound being separated and the extractive agent is desirable. It is also desirable that the extractive agent be miscible with isopropanol otherwise it will form a two phase azeotrope with the isopropanol in the recovery column and some other method of separation will have to be used, as well as having a deleterious effect on the extractive distillation.

The ratios shown in Table II are the parts by weight of extractive agent use per part of isopropyl ether-isopropanol-water azeotrope and the two relative volatilities correspond to the two different ratios. For example in Table II, one part of isopropyl ether-isopropanol-water azeotrope with one part of diethylene glycol methyl ether gives a relative volatility of 2.72, 6/5 parts of diethylene glycol methyl ether gives 2.17. One half part of diethylene glycol diethyl ether mixed with one half part of diethylene glycol ethyl ether with one part of isopropyl ether-isopropanol-water azeotrope gives a relative volatility of 2.01, 3/5 parts of diethylene glycol diethyl ether plus 3/5 parts of diethylene glycol ethyl ether gives 1.60.

Several of the compounds and mixtures listed in Table II and whose relative volatility had been determined in the vapor-liquid equilibrium still, were then evaluated in a glass perforated plate rectification column possessing 4.5 theoretical plates. The results are listed in Table III. The isopropyl ether-isopropanol-water mixture studied contained 10% isopropyl ether, 85% isopropanol, 5% water. The ternary azeotrope contains 88.0 wt.% isopropyl ether, 7.3 wt.% isopropanol and 4.7 wt.% water. What is remarkable is that pure isopropyl ether comes off as overhead product. In every case the feed or bottoms product contained less than 88% isopropyl ether and in every case the overhead is richer than 88% isopropyl ether. Without extractive distillation agents, the overhead would be the azeotrope, 88% isopropyl ether. This proves that the extractive agent is negating the azeotrope and makes the rectification proceed as if the azeotrope no longer existed and brings the more volatile component, isopropyl ether, out as overhead. It is our belief that this is the first time that this has been reported for this azeotrope.

The data in Table III was obtained in the following manner. The charge designated "blank" was 10% isopropyl ether, 85% isopropanol and 5% water and after 1.5 hours operation in the 4.5 theoretical plate column, the relative volatility of the separation between the isopropyl ether-isopropanol-water azeotrope and isopropanol was 3.28. The remaining data is for the extractive distillation agents designated. Here we have negated the azeotrope and brought out the pure isopropyl ether as overhead. The temperature of the overhead approaches 63° C., the boiling point of pure isopropyl ether at 630 mm. Hg.

OBJECTIVE OF THE INVENTION

The object of this invention is to provide a process or method of extractive distillation that will enhance the relative volatility of isopropyl ether from isopropanol and water in their separation in a rectification column. It is a further object of this invention to identify suitable extractive distillation agents which will eliminate the isopropyl ether-isopropanol-water azeotrope and make possible the production of pure isopropyl ether and isopropanol by rectification. It is a further object of this invention to identify organic compounds which, in addition to the above constraints, are stable, can be separated from isopropanol and water by rectification with relatively few plates and can be recycled to the extractive distillation column and reused with little decomposition.

SUMMARY OF THE INVENTION

The objects of this invention are provided by a process for separating isopropyl ether from isopropanol and water which entails the use of certain oxygenated organic compounds as the agent in extractive distillation.

DETAILED DESCRIPTION OF THE INVENTION

We have discovered that certain oxygenated organic compounds, some individually but principally as mixtures, will effectively negate the isopropyl ether-isopropanol-water azeotrope and permit the separation of oure isopropyl ether from isopropanol and water by rectification when employed as the agent in extractive distillation. Table II lists the compounds, mixtures and approximate proportions that we have found to be effective. The data in Table II was obtained in a vapor-liquid equilibrium still. In each case, the starting material was the isopropyl ether-isopropanol-water azeotrope. The ratios are the parts by weight of extractive agent used per part of isopropyl ether-isopropanol-water azeotrope. The relative volatilities are listed for each of the two ratios employed.

The compounds that are effective as extractive distillation agents when used alone are ethylene glycol hexyl ether, propylene glycol methyl ether, diethylene glycol methyl ether, diethylene glycol ethyl ether, diethylene glycol butyl ether, diethylene glycol diethyl ether, propylene glycol and ethylene glycol. The compounds that are effective when used in mixtures of two or more components are propylene glycol ethyl ether, diethylene glycol butyl ether and diethylene glycol hexyl ether.

TABLE II

Extractive Distillation Agents Which Are Effective In Separating Isopropyl Ether As Overhead From Isopropanol

| Compounds | Ratios | Relative Volatilities |
|---|---|---|
| Diethylene glycol methyl ether | 1 6/5 | 2.72 2.17 |
| Diethylene glycol ethyl ether | 1 6/5 | 3.55 2.30 |
| Ethylene glycol hexyl ether | 1 6/5 | 2.00 1.33 |
| Propylene glycol methyl ether | 1 6/5 | 1.72 1.35 |
| Diethylene glycol butyl ether | 1 6/5 | 1.55 1.46 |
| Diethylene glycol diethyl ether, Diethylene glycol ethyl ether | $(\frac{1}{2})^2$ $(3/5)^2$ | 2.01 1.60 |
| Diethylene glycol diethyl ether, Propylene glycol ethyl ether | $(\frac{1}{2})^2$ $(3/5)^2$ | 1.41 1.62 |
| Diethylene glycol butyl ether, Diethylene glycol hexyl ether | $(\frac{1}{2})^2$ $(3/5)^2$ | 1.10 1.52 |

TABLE III

Data From Runs Made In Rectification Column.

| Compounds | Overhead Temp. °C. | Phases in Overhead | Relative Volatility |
|---|---|---|---|
| Blank (no agent) | 56.8 | 2 | * |
| Diethylene glycol diethyl ether | 62.6 | 2 | 3.20 |
| Propylene glycol | 63.2 | 1 | 4.88 |
| Ethylene glycol | 62.2 | 2 | 5.18 |

Notes:
*did not negate the azeotrope
Feed composition was 50 gr. isopropyl ether, 425 gr. isopropanol, 25 gr. water.

THE USEFULNESS OF THE INVENTION

The usefulness or utility of this invention can be demonstrated by referring to the data presented in Tables II & III. All of the successful extractive distillation agents show that isopropyl ether can be removed from its ternary minimum azeotrope with isopropanol and water by means of distillation in a rectification column and that the ease of separation as measured by relative volatility is considerable. Without the extractive distillation agents, no improvement above the azeotrope composition will occur in the rectification column. The data also show that the most attractive agents will operate at a boilup rate low enough to make this a useful and efficient method of recovering high purity isopropyl ether from any mixture with isopropanol and water including the ternary minimum azeotrope. The stability of the compounds used and the boiling point difference is such that complete recovery and recycle is obtainable by a simple distillation and the amount required for make-up is small.

WORKING EXAMPLES

Example 1: The isopropyl ether-isopropanol-water ternary azeotrope is 88% isopropyl ether, 7.3% isopropanol and 4.7% water. Thirty grams of the isopropyl ether-isopropanol-water azeotrope and 30 grams of diethylene glycol methyl ether were charged to an Othmer type glass vapor-liquid equilibrium still and refluxed for 11 hours. Analysis of the vapor and liquid by gas chromatography gave vapor 97.3%, isopropyl ether, 2.7% isopropanol; liquid of 93% isopropyl ether, 7% isopropanol. This indicates a relative volatility of 2.72. Ten grams of the azeotrope were added and refluxing continued for another nine hours. Analysis indicated a vapor composition of 97.6% isopropyl ether, 2.4% isopropanol, a liquid composition of 94.8% isopropyl ether, 5.2% isopropanol which is a relative volatility of 2.17. The lower concentration of extractive agent gives a lower relative volatility as expected.

Example 2: Thirty grams of the isopropyl ether-isopropanol-water azeotrope, 15 grams of propylene glycol methyl ether and 15 grams of diethylene glycol diethyl ether were charged to the vapor-liquid equilibrium still and refluxed for six hours. Analysis indicated a vapor composition of 97.6% isopropyl ether, 2.4% isopropanol, a liquid composition of 96.7% isopropyl ether, 3.3% isopropanol which is a relative volatility of 1.41. Ten grams of the azeotrope were added and refluxing continued for another six hours. Analysis indicated a vapor composition of 97% isopropyl ether, 3% isopropanol, a liquid composition of 95.2% isopropyl ether, 4.8% isopropanol which is a relative volatility of 1.62.

Example 3: A glass perforated plate rectification column was calibrated with ethylbenzene and p-xylene which possesses a relative volatility of 1.06 and found to have 4.5 theoretical plates. A solution of 50 grams of isopropyl ether, 425 grams of isopropanol and 25 grams of water was placed in the stillpot and heated. When refluxing began, an extractive agent containing pure ethylene glycol was pumped into the column at a rate of 20 ml/min. The temperature of the extractive agent as it entered the column was 58° C. After establishing the feed rate of the extractive agent, the heat input to the isopropyl ether, isopropanol and water in the stillpot was adjusted to give a total reflux rate of 10–20 ml/min. After one hour of operation, overhead and bottoms samples of approximately two ml. were collected and analysed using gas chromatography. The ratio of isopropyl ether to isopropanol in the overhead was 97.98%. The ratio of isopropyl ether to isopropanol in the bottoms was 3.59%. Using these ratios in the Fenske equation, with the number of theoretical plates in the column being 4.5, gave an average relative volatility of 4.92. After 1.5 hours of operation, the overhead and bottoms samples were taken and analysed. The ratio of isopropyl ether to isopropanol in the overhead was 98.03%. the ratio of isopropyl ether to isopropanol in the bottoms was 2.94%. This gave an average relative volatility of 5.18. After two hours of total operating time, the overhead and bottoms samples were again taken and analysed. The ratio of isopropyl ether to isopropanol in the overhead was 97.9%, the ratio of isopropyl ether to isopropanol in the bottoms was 4.84%. This gave an average relative volatility of 4.55.

We have shown that by the use of the proper compound or combination of compounds as agents, isopropyl ether can be effectively removed from its mixture with isopropanol and water in any proportion including the minimum ternary azeotrope.

The nature of the present invention having been described, what we wish to claim as new and useful and secure by Letters Patent is:

1. A method for recovering isopropyl ether from a mixture of isopropyl ether, isopropanol and water which comprises distilling a mixture of isopropyl ether, isopropanol and water in a rectification column in the presence of about one part of extractive agent per part of isopropyl ether-isopropanol-water mixture, recovering isopropyl ether as overhead product and obtaining the extractive agent, isopropanol and water from the stillpot, the extractive agent comprises ethylene glycol.

2. A method for recovering isopropyl ether from a mixture of isopropyl ether, isopropanol and water which comprises distilling a mixture of isopropyl ether, isopropanol and water in a rectification column in the presence of about one part of extractive agent per part of isopropyl ether-isopropanol-water mixture, recovering isopropyl ether as overhead product and obtaining the extractive agent, isopropanol and water from the stillpot, the extractive agent comprises propylene glycol.

3. A method for recovering isopropyl ether from a mixture of isopropyl ether, isopropanol and water which comprises distilling a mixture of isopropyl ether, isopropanol and water in a rectification column in the presence of about one part of extractive agent per part of isopropyl ether-isopropanol-water mixture, recovering isopropyl ether as overhead product and obtaining the extractive agent, isopropanol and water from the stillpot, the extractive agent comprises a glycol ether containing from four to ten carbon atoms.

4. The method of claim 3 in which the extractive agent comprises diethylene glycol methyl ether.

5. The method of claim 3 in which the extractive agent comprises diethylene glycol ethyl ether.

6. The method of claim 3 in which the extractive agent comprises ethylene glycol hexyl ether.

7. The method of claim 3 in which the extractive agent comprises propylene glycol methyl ether.

8. The method of claim 3 in which the extractive agent comprises diethylene glycol diethyl ether and at least one material from the group consisting of diethylene glycol ethyl ether and propylene glycol ethyl ether.

9. The method of claim 3 in which the extractive agent comprises a mixture of diethylene glycol butyl ether and diethylene glycol hexyl ether.

* * * * *